United States Patent
Gern et al.

(10) Patent No.: US 6,187,332 B1
(45) Date of Patent: Feb. 13, 2001

(54) ACIDIC BUFFERED NASAL SPRAY

(75) Inventors: James E. Gern, Madison; Anne G. Mosser, Verona, both of WI (US)

(73) Assignee: Wisconsin Alumni Research Foundation, Madison, WI (US)

( * ) Notice: Under 35 U.S.C. 154(b), the term of this patent shall be extended for 0 days.

(21) Appl. No.: 09/332,340

(22) Filed: Jun. 14, 1999

(51) Int. Cl.⁷ ..................................................... A61K 9/00
(52) U.S. Cl. ........................... 424/434; 424/400; 424/422
(58) Field of Search ........................... 514/885; 222/206; 424/434

(56) References Cited

U.S. PATENT DOCUMENTS

| | | |
|---|---|---|
| 3,975,536 | 8/1976 | Stevenson et al. . |
| 4,689,223 * | 8/1987 | Arias ........................ 424/154 |
| 4,828,912 | 5/1989 | Hossain et al. . |
| 4,897,304 | 1/1990 | Hossain et al. . |
| 4,975,217 | 12/1990 | Brown-Skrobot et al. . |
| 5,026,825 * | 6/1991 | Grebow et al. ........................ 530/307 |
| 5,124,315 * | 6/1992 | Ceschel et al. ........................ 514/12 |
| 5,482,931 * | 1/1996 | Harris et al. ............................ 514/15 |
| 5,897,858 * | 4/1999 | Haslwanter et al. ............... 424/78.04 |
| 6,013,632 * | 1/2000 | Jones et al. ............................ 514/17 |

FOREIGN PATENT DOCUMENTS

| | | |
|---|---|---|
| 2103089 | 2/1983 | (GB) . |
| 85/00112 | 2/1985 | (WO) . |
| 93/18747 | 9/1993 | (WO) . |

OTHER PUBLICATIONS

"Nasal Washings Using A Neti Pot", undated two pages of description and instructions for use, admitted prior art, describing nasal solution with salty water having baking soda.

Copies of two labels from a packet of SinuCleanse™ (1997), by MedSystems, Inc.

A. Talbot et al., Mucociliary Clearance And Buffered Hypertonic Saline Solution, 107 Laryngoscope 500–503 (1997).

J. McLean et al., The Effects Of Topical Saline And Isoproterenol On Nasal Airway Resistance, 58 J. Allergy Clin. Immunol., 563–574 (1976).

* cited by examiner

Primary Examiner—Thurman K. Page
Assistant Examiner—P. E. McQueeney
(74) Attorney, Agent, or Firm—Quarles & Brady LLP

(57) ABSTRACT

Disclosed herein are buffered flowable nasal sprays having a pH of between 4.0 and 5.0. They are primarily water and a citrate (or citrate/phosphate) buffer. They may also contain sodium chloride, thickeners, and/or preservatives. The preparations are able to maintain the aforesaid pH under conditions simulating a runny nose. Methods of using these preparations to inhibit the spread of rhinovirus and/or diseases caused by rhinovirus are also disclosed.

10 Claims, No Drawings

ACIDIC BUFFERED NASAL SPRAY

STATEMENT REGARDING FEDERALLY SPONSORED RESEARCH

This invention was made with United States government support awarded by the following agency: NIH Grant No: AI40685. The United States has certain rights in this invention.

CROSS REFERENCES TO RELATED APPLICATIONS

Not applicable.

BACKGROUND OF THE INVENTION

The present invention relates to sprayable nasal preparations which are designed to suppress rhinovirus. More particularly, it relates to buffered acidic solutions that are capable of being sprayed into a human nose and maintaining a defined pH in vivo.

Physicians have often prescribed nasal sprays to treat a variety of nasal symptoms. For example, in A. Talbot et al., 107 Laryngoscope 500–503 (1997) the authors discuss using normal or hypertonic buffered alkaline saline solutions as nasal sprays. These sprays are usually intended to treat the symptoms of a variety of nasal conditions (e.g. sinusitis).

A few mildly acidic nasal sprays are also known. Atrovent® nasal spray has a pH of about 4.7 and is believed to contain an anticholinergic agent (ipratropium bromide monohydrate), preservatives benzalkonium chloride and sodium EDTA, sodium chloride, sodium hydroxide, hydrochloric acid, and water. However, the solution is not buffered to maintain a low pH in the nose over prolonged periods.

Similarly, NasalCrom® nasal spray has a pH of 4.5–6.0 and is believed to contain cromolyn sodium in water and preservatives. Again, when challenged with even moderate dilution (with an essentially neutral pH solution), the formulation quickly reaches a neutral pH.

A product called ZICAM nasal spray (GumTech Industries) is currently claiming to reduce the effects and duration of common colds. It contains zincum gluconium in an unbufferred pH 6.7 spray solution. The effectiveness of the spray is still being evaluated. However, in any event, it requires the use of an expensive ingredient.

Other sprays and oral preparations are known that are designed to inhibit viral replication, and thereby moderate colds if given shortly before or shortly after exposure. However, such preparations again rely on the use of expensive components (e.g. ICAM-1).

The virus believed responsible for most of the symptoms attributable to a "common cold", rhinovirus, is known to be sensitive to substantially acidic pH conditions. However, this knowledge has not, to date, led to a practical therapy or technique for controlling common cold infection.

For one thing, many parts of the human body are sensitive to highly acidic conditions and will not tolerate prolonged contact with those conditions. Further, many materials (e.g. many buffers) that are acidic are not otherwise suitable for contact with a human. For example, acetates often provide an undesirable vinegar taste, ascorbates often oxidize to undesirable colors, aspartates, glutamates, and tartrates do not have desirable solubility characteristics, borates and phthalates have toxic side effects, formates don't buffer in the right pH range, and propionates and succinates produce a burning sensation.

Moreover, apart from the desirability of providing temporary symptomatic relief to a person that is infected with a virus, there is a desire (a) to inhibit the tendency of that person to spread the infection to others, (b) for persons who do not have the infection to have a preparation which will reduce the likelihood of their catching the infection from someone who has it, and (c) for there to be a way to reduce the severity and duration of the infection once it is caught. It is particularly desirable that these goals be achieved at low cost and using techniques that are well tolerated by patients.

As such, it can be seen that the need exists for an improved nasal spray and methods of using it.

BRIEF SUMMARY OF THE INVENTION

In one aspect the invention provides a buffered flowable nasal preparation having a pH of between 4.0 and 5.0. It contains water (preferably 95–98 weight percent) and a citrate (preferably 0.02 M citrate anion to 0.06 M citrate anion). The "citrate" can be provided by citric acid or an alkali metal citrate such as sodium citrate. There may also be phosphate (preferably 0.03 M phosphate cation to 0.09 M phosphate cation).

In accordance with the present invention the preparation is sufficiently buffered so as to be able to maintain a pH below 6.0 when challenged in the "Buffering Power" test described below. In this test a given volume of the preparation is mixed at room temperature with three times that volume of Dulbecco's phosphate buffered saline (pH 7.4) (sold by Fisher Scientific—currently Pittsburgh, Pa.). The pH of the resulting solution is tested and the test is passed if the resulting solution has a pH below 6.0.

This test simulates pH changes via dilution that might be expected when a nasal spray is squirted into a runny nose. Normal nose mucus and snot have an essentially neutral pH and would tend to quickly render prior art nasal sprays neutral.

In preferred aspects the preparation is a nasal spray containing between 0 and 0.5 weight percent of sodium chloride and a cellulosic thickener. One preferred cellulosic thickener is methyl cellulose at 0.25 to 1.0 weight percent of the composition. Other possible cellulosic thickeners are microcrystalline cellulose and hydroxyethyl cellulose. The thickener helps the nasal spray to adhere to the inside of the nose (so that it is less likely to be blown away by sneezing or by blowing of the nose).

A particularly desirable buffering system is one containing both citrate and phosphate. While phosphate alone has too high a pH, it adds desirable buffering characteristics when mixed with citrate. It is also desirable to include one or more standard nasal spray preservatives such as benzalkonium chloride and/or EDTA/sodium EDTA.

In other aspects the invention provides methods for:
(a) killing rhinovirus virus by exposing the rhinovirus to the above preparations;
(b) killing rhinovirus virus in a human nose by spraying the above preparations into the nose; and
(c) inhibiting the spread of rhinoviral infection by spraying the above preparations into either an uninfected or infected human's nose.

The present invention provides improved nasal sprays that can kill rhinovirus in the human nose. This reduces the likelihood of those who come near an infected person becoming infected, and may thus provide a prophylactic treatment for those who are not infected who use the spray. Also, this hopefully will help reduce the duration and severity of symptoms for those already infected.

The objects of the present invention therefore include providing:
(a) nasal sprays of the above kind;
(b) nasal sprays which can retain a pH of between 4 and 5.5 (preferably 5.0) for prolonged periods in a human nose; and
(c) methods of using these nasal sprays to reduce the spread, severity and duration of diseases caused by rhinovirus.

These and still other objects and advantages of the present invention will be apparent from the description which follows. The following description is merely of the preferred embodiments. Thus, the claims should be looked to in order to understand the full scope of the invention.

DETAILED DESCRIPTION

We initially tested various preparations within the scope of the claims to confirm in vitro that they killed rhinovirus. We mixed rhinovirus with the claimed preparation and monitored the rhinovirus titer at various times and temperatures. We determined that the lower the pH, the greater the killing effect of the solutions, that the claimed compounds killed the rhinovirus, and further that the killing effect was more pronounced at about human body temperature than at about room temperature.

In this regard, we tested the effect of low-pH buffers on the rhinovirus RV16's viability. $10^7 TCID_{50}/ml$ was diluted into buffers pre-equilibrated to either room temperature or 35° C. At intervals, 10 μL samples were transferred to tubes containing 1 mL of chilled PBS with 0.1% albumin (PBSA). Quantitative viral titers were then performed.

We then tested the effect of our preparations on RV16 replication in non-transformed cells such as primary bronchial epithelial cells isolated from lungs. Our preparations were very effective in reducing virus titer.

In our next series of tests we examined a variety of citrate and citrate/phosphate buffers for their characteristics. We found that both citrate and citrate/phosphate buffers provided desirable acid and buffering capabilities without causing adverse damage to epithelial cells in vitro.

We then ran a clinical test on humans to evaluate tolerance. No major side effects were reported.

Our preferred preparations to date are as follows (gm/L):

|  | Formula 1 | Formula 2 | Formula 3 |
|---|---|---|---|
| Citric acid | 10.46 | 5.23 | 12.68 |
| $Na_2PO_4 \cdot 7H_2O$ | 24.42 | 12.21 | — |
| methylcellulose | 5.00 | 5.00 | 5.00 |
| benzalkonium Cl | .01 | .01 | .01 |
| EDTA | 1.00 | 1.00 | 1.00 |
| NaCl | — | 4.38 | — |
| sodium citrate | — | — | 27.70 |

Our preparations rapidly inactivate rhinovirus, retain low pH even after substantial dilution, have low toxicity, are well tolerated in experiments to date, mostly use materials that have been previously approved in connection with human contact, are inexpensive to produce, and are simple to use.

It should be recognized that protocols for using these preparations may be optimized depending upon the degree of existing infection, the age of the patient, and whether the preparation is being used prophylactically or to treat an existing condition. However, for most conditions we suggest spraying in the nose 0.2 to 0.3 ml of the preparation in each nostril, three to six times daily, for five days.

The effect is believed to work across a wide variety of rhinovirus, including rhinovirus associated with common cold effects.

INDUSTRIAL APPLICABILITY

The invention provides preparations for inhibiting the spread and development of rhinoviral infection.

We claim:

1. A method of killing rhinovirus virus in a human nose comprising spraying a preparation into the nose, wherein preparation comprises:
   a buffered flowable nasal preparation having a pH of between 4.0 and 5.0, comprising water, and a citrate, wherein the preparation is sufficiently buffered so as to be able to maintain a pH below 6.0 when challenged under the "Buffering Power" test.

2. A method of inhibiting the spread of rhinoviral infection comprising spraying a preparation into a human's nose, wherein preparation comprises:
   a buffered flowable nasal preparation having a pH of between 4.0 and 5.0, comprising water, and a citrate, wherein the preparation is sufficiently buffered so as to be able to maintain a pH below 6.0 when challenged under the "Buffering Power" test.

3. The method of claim 1, wherein the preparation is a nasal spray.

4. The method of claim 1, wherein the preparation also comprises sodium chloride.

5. The method of claim 4, wherein sodium chloride is present in the preparation and the concentration of sodium chloride is 0.5 weight percent of the preparation or less.

6. The method of claim 1, wherein the preparation further comprises a cellulosic thickener.

7. The method of claim 1, wherein the preparation also comprises a phosphate.

8. The method of claim 1, wherein the preparation also comprises a preservative selected from the group consisting of benzalkonium chloride and sodium EDTA.

9. The method of claim 1, wherein the concentration of citrate anion is at least 0.02 M.

10. The method of claim 1, wherein the concentration of water is at least 95 weight percent of the preparation.

* * * * *